United States Patent [19]

Freedman

[11] 4,185,634
[45] Jan. 29, 1980

[54] SURGICAL INSTRUMENT

[76] Inventor: Bruce M. Freedman, 70 Brook Rd., Milton, Mass. 02187

[21] Appl. No.: 864,280

[22] Filed: Dec. 27, 1977

[51] Int. Cl.² ............................................. A61B 17/32
[52] U.S. Cl. ...................................... 128/314; 30/353
[58] Field of Search .................. 128/305, 314; 30/346, 30/353, 357, 32

[56] References Cited

U.S. PATENT DOCUMENTS

| 298,047 | 5/1884 | Webb | 30/353 |
|---|---|---|---|
| 1,820,234 | 8/1931 | Lees | 30/357 |
| 1,997,953 | 4/1935 | Kuy | 30/346 |
| 2,649,860 | 8/1953 | Royer | 128/314 |
| 2,838,049 | 6/1958 | Eisenhofer | 128/305 |
| 3,276,120 | 10/1966 | Scott | 128/305 |

FOREIGN PATENT DOCUMENTS

| 156651 | 1/1964 | U.S.S.R. | 128/305 |
|---|---|---|---|
| 387703 | 9/1973 | U.S.S.R. | 128/305 |

*Primary Examiner*—Richard J. Johnson
*Attorney, Agent, or Firm*—Wolf, Greenfield & Sacks

[57] ABSTRACT

A surgical blade used for incisions and other surgical operations to be performed in a narrow space or area such as minor surgery that may be performed on the joints and tissues of the foot. The instrument comprises a stem portion which may be received by a handle for holding the instrument, and a blade portion connected from the stem portion and terminating in a tip. The surgical blade is preferably for surgery requiring an incision in the skin followed by cutting of contracted muscle tendon attaching members such as planter aponeuroses with the blade portion having a cutting edge on one side and an incising edge contiguous with the cutting edge formed about the tip and extending partially along the other side of the instrument. The preferred length of the blade portion is on the order of 5–10 millimeters while the preferred width is on the order of 1–3 millimeters.

6 Claims, 5 Drawing Figures

U.S. Patent     Jan. 29, 1980     4,185,634
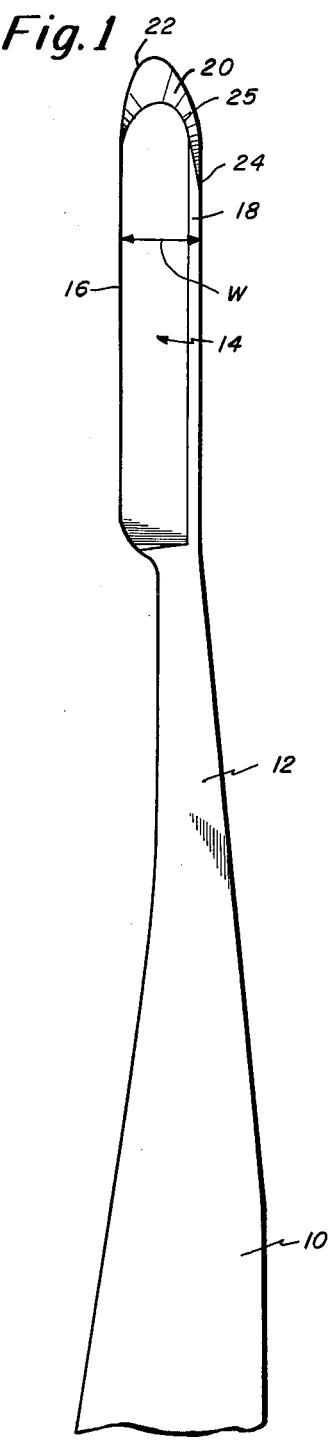
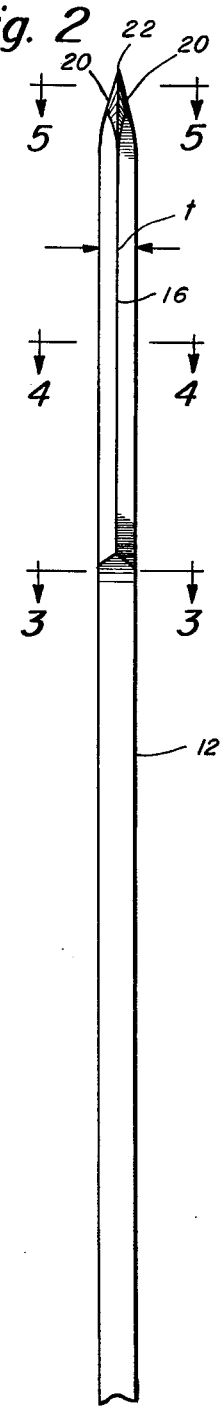
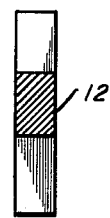
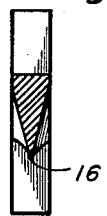
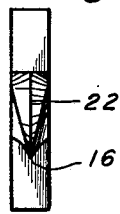

SURGICAL INSTRUMENT

BACKGROUND OF THE INVENTION

The present invention relates in general to surgical blades and more specifically to an improved surgical blade construction preferably for use in surgery in confined areas or spaces such as in the joints and tissues of the foot or hand. The instrument of this invention is particularly for use in relieving the crippling effects in the feet due to contractions of the dorsal and plantar muscle-tendon-ligament aponeuroses.

In the prior art a conventional type of surgical blade is shown in, for example, the Lowe U.S. Pat. No. 2,029,495. A surgical blade is also shown in the Royer U.S. Pat. No. 2,649,860 adapted particularly for surgery in the hands. The conventional surgical blade is generally too large and not well adapted for use in podiatric applications and with the conventional blade there is too much of an opportunity for damage to the tissue adjacent to the fibrous band which is to be cut. Although the Royer construction is an improvement over conventional surgical blades there still are disadvantages associated therewith and particularly when the blade is to be used for podiatric applications.

The surgical blade of this invention, although preferably used for podiatric applications, may also be used in other types or surgery, especially those requiring incision, insertion of the blade through the incision and the cutting of a fibrous band such as a contracted aponeuroses.

Accordingly, one object of the present invention is to provide a surgical blade of improved construction and particularly adapted for the uses set forth hereinbefore.

Another object of the present invention is to provide a surgical blade which is of extremely small dimensions and which is narrow enough to fit into joints of the foot and which is yet strong enough to cut ligaments and tendons.

A further object of the present invention is to provide a surgical blade having a blade portion preferably of a length on the order of 5-10 millimeters and a width preferably on the other of 1-5 millimeters.

Still another object of the present invention is to provide a surgical blade that is very thin having a thickness of 1 millimeter or preferably less having a linear cutting edge contiguous with an incising edge at the tip extending in a substantially U-shape partially on the opposite side of the blade permitting the forming of an incision through which the entire cutting edge of the blade may easily be slid.

Still another object of the present invention is to provide a surgical blade preferably sharpened only along its cutting edge and incising edge but dulled on the remainder of the opposite side to minimize damage to, for example, nerves or veins that may be adjacent to the fibrous bands that are being severed.

Another object of the present invention is to provide a surgical blade that is dimensioned to make an incision that is extremely narrow with the results that few if any blood vessels are punctured thereby providing very clean surgery with little or no bleeding along the incision.

Still a further object of the invention is to provide a surgical blade that is capable of incision and cutting with relatively little after effect upon the patient.

SUMMARY OF THE INVENTION

To accomplish the foregoing and other objects of this invention there is provided a surgical instrument which comprises a stem portion and a blade portion extending from the stem portion. Both the stem and blade portions may be constructed of surgical stainless steel. The stem portion is adapted for fitting in a handle for the purpose of holding the instrument. The blade portion of the surgical instrument is elongated and has a linearly extending cutting edge along one side thereof. This cutting edge may have a length in the range of 5-10 millimeters. The blade portion also has formed therein an incising edge at the tip of the blade portion which is contiguous with the cutting edge of the blade portion extending arcuately about the tip partially along and terminating at the other side of the blade portion. The width of the blade portion is preferably in the range of 1-5 millimeters while the thickness of the blade portion is preferably in the range of 0.25-1 millimeter. With the blade of these dimensions it is possible to have dramatic improvements in the surgical techniques that are used especially for surgery involving the hands or feet.

Many podiatric patients are found to be crippled by shrinkage or contraction of the tendons, ligaments, or aponeuroses (flat sheets of connective tissue) connecting their muscles and foot bones. This tends to cause the toes and arches to curl up, making walking on the Metatarsal heads painful. This disorder can be relieved with the proper use of the improved surgical blade of this invention. Initially, a local anesthetic is injected into the skin near the connective tissue which is to be cut. The anesthetic substance is also deposited along the line where the incision is to be made. The incising edge of the blade is used to make an incision in the skin just long enough to admit substantially the entire length of the blade portion. With the toes held in either flexion or extension, the blade portion is inserted into the incision and the cutting edge extends the incision along the previously anesthetized line. The side of the blade is maintained parallel to the skin with the incising edge used to separate the muscle-tendon ligament either over or between the metatarsal-interphalangeal oints. Thereafter the cutting edge is used to sever the aponeurosis. After the fibers have been severed the instrument is then withdrawn and the incision is closed. It has been found in accordance with the invention that stitches are not necessary because of the extremely fine incision that is made with the instrument of this invention. Also, the healing of the incision occurs quite rapidly and after a period of say 2-5 days, the incision is not even discernible.

DESCRIPTION OF THE DRAWINGS

Numerous other objects, features and advantages of the invention should now become apparent upon a reading of the following detailed description taken in conjunction with the accompanying drawings, in which:

FIG. 1 is a side elevational view of a surgical instrument of this invention;

FIG. 2 is an elevation view as viewed along the cutting edge of the same instrument as shown in FIG. 1;

FIG. 3 is a cross-sectional view taken along line 3—3 of FIG. 2;

FIG. 4 is a cross-sectional view taken along line 4—4 of FIG. 2; and

FIG. 5 is a cross-sectional view taken along line 5—5 of FIG. 2.

DETAILED DESCRIPTION

FIGS. 1-5 show a preferred embodiment of the present invention of a surgical blade comprising a flat shank 10 which tapers via neck 12 to the blade 14. The blade 14 has on one side a sharp cutting edge 16 which extends linearly, and on the other side a dulled edge 18 which also extends linearly as depicted in FIG. 1. The blade 14 terminates in a tip 20 having formed thereat an incising edge 22 which is contiguous with the cutting edge 16. The edge 22 extends in a U-shape as depicted in FIG. 1 terminating on the other side of the blade at point 24. The cutting edge 16 and the incising edge 22 extend in a like plane.

The neck 12 has a rectangular cross-section as shown in FIG. 3. Similarly, the flat shank 10 also has a rectangular cross-section and has a length sufficient to permit the shank to be received by a conventional handle for the instrument. The blade portion of the device may have a length on the order of 5-10 millimeters. The width w of the blade portion may be in the range of 1-5 millimeters while the thickness t as shown in FIG. 2 may be in the range of 0.25-1 millimeter. The section 25 of the incising edge preferably extends at least 1 millimeter from the very tip of the edge to the terminating point 24. With these width and thickness dimensions the surgical blade is used with great ease between bones of the foot joints.

The surgical blade of this invention is used in a surgical technique for relieving the crippling effect caused by contractions of the dorsal and plantar muscle-tendon-ligament aponeuroses. The contraction of these fiber bands causes curling and attendant pain in the feet. In order to relieve this crippling effect these fibrous bands are severed. Initially, a local anesthesia is injected at a relatively small area of the skin close to the aponeuroses that is to be incised. This anesthetic agent is also injected along the course that the incision is to take. The incising edge 22 of the blade 14 is used to initially make a very small incision in the skin sufficiently large to permit the blade to be inserted through the incision. The toes are then held in either an extension or flexion position and the cutting edge 16 is used to make an incision along the previously anesthetized course. The incising edge is used to separate the muscle-tendon-ligament either over or between the metatarsal-interphalangeal joints. The blade is then rotated to engage the fibrous band that is to be cut. The toe is then forcibly extended or flexed thus stretching the fibrous band. The fibrous band is then severed by the cutting edge 16. The blade may then be returned to its parallel relationship with regard to the skin and withdrawn from the incision.

The surgical procedure may be repeated a number of times in order to relieve the crippling effect. It has been found that with the blade of this invention the wound heals quite readily. The patient suffers little or no discomfort and is able to support his weight on the foot immediately after the operative procedure and is able to leave the office.

The surgical blade of this invention may also be used in vascular, neurological, plastic, oto and pothomological types of surgery where a fine exact instrument is needed providing complete control and exactness of technique. The instrument may also be used on patients whose circulatory status may be questionable, or where they have a severe limiting disease where these individuals may not otherwise have the opportunity to have correction of their disorder. Also, having in-office surgery cuts costs to the patient and hospital with the patient going home immediately after the surgery.

What is claimed is:

1. A surgical instrument comprising:
   a stem portion, and
   a blade portion extending from the stem portion,
   said blade portion being elogated having a linearly extending cutting edge along one side thereof and an incising edge at the tip of the blade portion contiguous with the cutting edge and extending arcuately in a U-shape about the tip partially along and terminating at the other side of the blade portion,
   the cross-section of the blade portion along the cutting edge being beveled on said one side and flat dull edged on said other side except at the incising edge,
   the major length of said other side of said blade portion being dulled and generally parallel to the cutting edge,
   the width of said blade portion being on the order of 1-3 millimeters,
   the thickness of said blade portion being on the order of 0.25-1.0 millimeter, and
   the length of the incising edge extending about the other side of the blade portion being at least 1 millimeter but less than the total length of the blade portion.

2. A surgical instrument as set forth in claim 1 wherein said cutting edge has a length on the order of at least 5 millimeters.

3. A surgical instrument as set forth in claim 2 wherein said cutting edge has a length in the range on the order of 5-10 millimeters.

4. A surgical instrument as set forth in claim 1 wherein the width of said blade portion is greater than the thickness and the length is greater than the width.

5. A surgical instrument as set forth in claim 4 wherein said width is at least on the order of twice the thickness and said length is at least on the order of twice the width.

6. A surgical instrument as set forth in claim 1 wherein said stem portion tapers from a larger width to a smaller width at the stem, blade connection with the smaller width being less than the width of the blade portion.

* * * * *